United States Patent [19]

Binder et al.

[11] 4,405,783

[45] Sep. 20, 1983

[54] PROCESS FOR THE PRODUCTION OF DIHYDROXYPROPYLTHEOPHYLLINE

[75] Inventors: Volker Binder, Gelnhausen; Wolfgang Merk, Hanau; Peter Werle, Gelnhausen, all of Fed. Rep. of Germany

[73] Assignees: Degussa Aktiengesellschaft, Frankfurt, Fed. Rep. of Germany; Degussa Aktiengesellschaft, Frankfurt, Fed. Rep. of Germany

[21] Appl. No.: 388,464

[22] Filed: Jun. 14, 1982

[30] Foreign Application Priority Data

Aug. 25, 1981 [DE]  Fed. Rep. of Germany ....... 3133553

[51] Int. Cl.$^3$ ............................................. C07D 473/08
[52] U.S. Cl. ........................................ 544/267; 424/253
[58] Field of Search ......................... 424/253; 544/267;

[56] References Cited

U.S. PATENT DOCUMENTS 2,575,344  11/1951  Jones et al. ......................... 544/267
4,031,218  6/1977  El-Antably .......................... 544/267

FOREIGN PATENT DOCUMENTS 482546  4/1952  Canada ................................ 544/267
1235927  3/1967  Fed. Rep. of Germany .
756594  9/1956  United Kingdom .

OTHER PUBLICATIONS

Maney, J. American Pharm. Assoc. vol. 35, pp. 266-272 (1946).
Samejima, Yakugarku Zasski vol. 80, pp. 1706-1723 (1960).
Chem. Abst. vol. 54, 11648g-11649.
Chem. Abst. vol. 55, 10439i.
Ishay, J. Chem. Soc. (London) 1956 (3975).
Auslander, Sci. Pharm. Proc. 25th-(1966) pp. 75-77.
Roth, Archiv der Pharmazie 292/64234 (1939).

*Primary Examiner*—Nicholas S. Rizzo
*Attorney, Agent, or Firm*—Cushman, Darby & Cushman; Cushman, Darby & Cushman

[57] ABSTRACT

Pure hydroxypropyltheophylline is produced by the catalytic reaction of theophylline with glycidol in the presence of a hydroxide of a short chain alcoholate of an alkali metal or an alkali metal salt of a pseudohydrohalic acid which has a readily polarizable anion. The catalyst is suitably employed in an amount between 0.01 and 0.2 moles per mole of theophylline. The dihydroxypropyltheophylline is obtained directly in the reaction in a high purity.

18 Claims, No Drawings

PROCESS FOR THE PRODUCTION OF DIHYDROXYPROPYLTHEOPHYLLINE

BACKGROUND OF THE INVENTION

Theophylline (1,3-dimethyl xanthine) and related natural materials are used pharmacologically because of their activities on the central nervous system and the heart circulation function. Theophylline has an outstanding action in status asthmaticus and bronchial asthma. The water solubility which is only slight and consequently the slow resorption can be improved substantially by converting it into suitable water soluble derivatives.

The dihydroxypropyltheophylline [1,3-dimethyl-7-(α, -dihydrohydroxpropyl)-xanthine] represents such a water soluble derivative. Its production is described e.g. by P. V. Maney et al in J. Amer. Pharm. Assoc. Vol. 35 pages 266–272 (1946) through reaction of theophylline with 3-chloro-1,2-dihydroxypropane (glycerine- α-monochlorohydrin) in the presence of an equivalent amount of aqueous sodium hydroxide. Several additional publications likewise describe the reaction of theophylline and glycerin-α-monochlorohydrin in the presence of KOH or NaOH (F. F. Auslander, Sci. Pharm. Proc. 25th, 1965, 1, 75-7; Jones U.S. Pat. No. 2,575,344; M. Samejima, Yakugarku Zasski Vol. 80 pages 1706–1723 (1960); see also Chem. Abst. Vol. 54 page 11648g and Chem. Abst. Vol. 55 page 10439i). D. Ishay recommends the reaction of theophylline with KOH in water with subsequent evaporation to dryness. Subsequently there takes place the addition of glycerine-α-monochlorohydrin and methanol. Yield 78% of melting point 155° to 158° C. (J. Chem. Soc. (London), page 3975 (1956)).

Most of the processes mentioned operate in aqueous medium with subsequent evaporation and recrystallization from methanol. Above all the disadvantage is the large amount of energy required which is due to the high vaporization enthalpy of water, as well as the accumulation of sodium chloride (0.230 kg/kg of dihydroxypropyl theophylline), which must be carefully and quantitatively separated from the reaction product.

A substantial improvement of the process results from the replacement of glycerine-α-monochlorohydrin by glycidol since in this case it is possible to work with small amounts of catalytically acting materials, the separation of large amounts of NaCL thus is eliminated. Besides it is possible to carry out the reaction in suitable solvents.

In Arch. Pharmaz. Ber. dt. pharmz. Ges. 292/64, 234 (1939) H. J. Roth reports on the reaction of theophylline and theobromine with 1,2-epoxides and employs as catalysts among others pyridine bases. The preferred solvent is n-propanol. In repeating these directions on a large scale it has been shown that a strong coloration of the reaction solution occurs through the pyridine, which coloration can only be eliminated by large amounts of activated carbon and furthermore the content of pyridine is very high (10% based on the theophylline employed). This leads to increased expense for apparatus in the purification of the mother liquors.

Besides the preparation obtained itself is of unsatisfactory purity after two recrystallizations (Roth gives a melting point of 154° to 155° C.) and the yield is not satisfactory, about 60% of theory based on theophylline.

The object of the invention is to develop a process for the production of dihydroxypropyltheophylline using glycidol and theophylline in which the reaction product not only is obtained in good yields but also in high purity.

SUMMARY OF THE INVENTION

It has now been found that this problem can be solved by carrying out the known reaction of theophylline with glycidol in the presence of a hydroxide or short chain alcoholate of an alkali metal or an alkali metal salt of a pseudohydrohalic acid which has a readily polarizable anion as catalyst.

As alkali metals above all there can be employed lithium, sodium and potassium. Sodium is especially preferred. Of the alcoholates (alkanoates) the methylate or ethylate have proven particularly favorable. However, there can also be used for example the propylate, isopropylate or butylate.

Under the term pseudohydrohalic acid which has a readily polarizable anion there is understood hydrogen cyanide (HCN); thiocyanic acid (HSCN), cyanic acid (HOCN), hydrazoic acid (HN$_3$), cyanamide (H$_2$N-CN) and dicyanimide

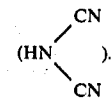

Especially preferred are the alkali hydroxides, e.g. lithium hydroxide and potassium hydroxide, above all sodium hydroxide, besides the cyanates, above all sodium cyanate or cyanamides as, e.g sodium cyanamide. Other illustrative compounds include sodium cyanide, potassium cyanide, sodium thiocyanate, potassium thiocyanate, lithium thiocyanate, lithium cyanide, potassium cyanate, lithium cyanate, sodium azide, potassium azide, potassium cyanamide, sodium dicyanimide and potassium dicyanimide.

The amounts of catalyst employed lie between 0.01 to 0.02 mole per mole of theophylline, preferably at 0.05 to 0.14 mole per mole of theophylline. As solvent for the reaction there can be employed water or a short chain alcohol such as methanol, ethanol, propanol or isopropanol. The alcohols can also be employed as aqueous products having a water content up to 20 weight % for example. Especially preferred is methanol since dihydroxypropyltheophylline has good solubility therein at the boiling temperature.

Theophylline and glycidol are employed in stoichiometrical amounts, preferably, however, with a slight excess of glycidol up to about 10 mole %.

Preferably operation is carried out in concentrated solution. It has proven favorable to use, e.g., concentrations of materials added of about 4 moles per liter of solvent. However, it is also possible to operate objection-free with molar amounts up to 6.5 moles. If in certain cases the filtering off with suction of the crystallized product from the reaction medium should be difficult then there can be produced in known manner suspensions which are suction filterable by adding solvents of lower density such as the above-mentioned alcohols in the cold without loss of yield.

It has proven favorable to carry out the reaction between theophylline and glycidol over a long interval of time, e.g. 3 to 5 hours, since through this there is reduced the danger of by-product formation.

In order to keep the concentration of glycidol low in the reaction medium, it is best to drop the glycidol into the boiling theophylline suspension. Glycidol and theophylline are employed in commercial quality. The reaction solutions are only colored weakly yellow in use of alkali metal hydroxides, otherwise they are colorless.

There are various possibilities for recovery of the dihydroxypropyltheophylline from the reaction solution, either the reaction can be cooled to low temperatures of, e.g. 0° C. or, in using alcohols as the solvent, a portion of this solvent can be distilled off and the crystallization carried out with stirring at, e.g. room temperature.

Dihydroxypropyltheophylline is obtained in yields of 85 to far above 90%, based on the theophylline employed, see the examples.

The purity of the reaction product is high; inter alia the portion of unreacted theophylline is 0.1 to 0.4 weight %; if absolutely necessary the purity can be still further increased by a customary recrystallization, e.g., from methanol.

As the examples show, the melting point of the dihydroxypropyltheophylline is between 161° and 164° C., after recrystallization at exactly 164° C. Herewith the product corresponds exactly to the requirements of the appropriate pharmacopeia.

The residual dihydroxypropyltheophylline obtained in the concentration of the mother liquor is likewise obtained in sufficient purity by recrystallization.

Unless otherwise indicated all parts, and percentages are by weight.

The process can comprise, consist essentially of or consist of the stated steps with the recited materials.

The invention is explained further in the following examples.

DETAILED DESCRIPTION

Example 1

108 grams (0.6 mole) of theophylline and 2.4 grams (0.06 mole) of NaOH were suspended in 320 ml of methanol and heated to boiling under reflux. Within 5 hours 49 grams (0.66 mole) of glycidol were dropped in and after the end of the addition of glycidol the clear, weakly yellow solution was stirred for a further 30 minutes. Through cooling to 0° C. under stirring, filtering and washing with methanol there were obtained 142.6 grams (92.6% of theory based on the theophylline employed) of dihydroxypropyltheophylline having a melting point of 162° to 164° C.

Example 2

108 grams (0.6 mole) of theophylline were suspended with 1.6 grams (0.04 mole) of NaOH in 320 ml of methanol and then processed in a manner analogous to Example 1. Yield 141.8 grams (92.1% of theory), Melting point 162° to 163° C.

Example 3

The example was carried out in a manner analogous to Example 1. As catalyst there was employed 6.48 grams (0.08 mole) of potassium cyanate. Yield 142.95 grams (93.8% of theory), Melting point 162° C.

Example 4

The example was carried out in a manner analogous to Example 3.

As catalyst there was employed 5.1 grams (0.08 mole) of sodium cyanamide.

Yield 135.6 grams (89.2% of theory), Melting point 161° to 162° C.

Example 5

108 grams (0.6 mole) of theophylline were treated with 2.4 grams (0.06 mole) of NaOH and treated with 150 ml of water. After heating to 90° C. under stirring 49 grams (0.66 mole) of glycidol were dropped in within 5 hours and allowed to post react about 30 minutes.

The mixture was slowly cooled under intensive stirring, filtered and the crystal sludge obtained filtered off with suction and washed with alcohol.

Yield 129.6 grams (85% of theory), Melting point 163° to 164° C.

Example 6

The product produced according to Example 4 was recrystallized from methanol or aqueous methanol. For this purpose 100 grams in 250 ml of methanol (90%) were heated to boiling, filtered and crystallized with stirring. Yield 89.5% of theory, Melting point 164° C.

The entire disclosure of German priority application P3133553.5 is hereby incorporated by reference.

What is claimed is:

1. In a process for the production of pure dihydroxypropyltheophylline by the catalytic reaction of glycidol and theophylline the improvement comprising carrying out the process in the presence of a catalyst which is a hydroxide or short chain alcoholate of an alkali metal or an alkali metal salt of a pseudohydrohalic acid which has a readily polarizable anion, the amount of catalyst being 0.01 to 0.2 mole per mole of theophylline.

2. A process according to claim 1 wherein the pseudohydrohalic acid is HCN, HOCN, HN$_3$, H$_2$N-CN or

3. A process according to claim 1 wherein there is employed a solvent which is water, a lower alkanol or a mixture thereof.

4. A process according to claim 1 wherein the catalyst is employed in an amount of 0.05 to 0.14 mole per mole of theophylline.

5. A process according to claim 1 wherein the catalyst is sodium hydroxide.

6. A process according to claim 4 wherein the catalyst is sodium hydroxide.

7. A process according to claim 1 wherein the catalyst is an alkali metal salt of hydrocyanic acid, thiocyanic acid, cyanic acid, hydrazoic acid, cyanamide or dicyanimide.

8. A process according to claim 4 wherein the catalyst is an alkali metal salt of hydrocyanic acid, thiocyanic acid, cyanic acid, hydrazoic acid, cyanamide or dicyanimide.

9. A process according to claim 7 wherein the catalyst is sodium cyanate or sodium cyanamide.

10. A process according to claim 8 wherein the catalyst is an alkali metal salt of hydrocyanic acid, thiocyanic acid, cyanic acid, hydrazoic acid, cyanamide or dicyanimide.

11. A process according to claim 3 wherein the solvent is water, methanol or a mixture thereof.

12. A process according to claim 11 wherein the catalyst is employed in an amount of 0.05 to 0.14 mole per mole of theophylline.

13. A process according to claim 11 wherein the catalyst is sodium hydroxide.

14. A process according to claim 12 wherein the catalyst is sodium hydroxide.

15. A process according to claim 11 wherein the catalyst is an alkali metal salt of hydrocyanic acid, thiocyanic acid, cyanic acid, hydrazoic acid, cyanamide or dicyanimide.

16. A process according to claim 15 wherein the catalyst is employed in an amount of 0.05 to 0.14 mole per mole of theophylline.

17. A process according to claim 1 wherein the catalyst is an alkali metal hydroxide.

18. A process according to claim 1 wherein the catalyst is an alkali metal short chain alkanoate.

* * * * *